(12) United States Patent
Fernandez Dell Oca

(10) Patent No.: US 8,660,331 B2
(45) Date of Patent: Feb. 25, 2014

(54) METHOD AND A SYSTEM FOR ASSESSING THE RELATIVE POSE OF AN IMPLANT AND A BONE OF A CREATURE

(75) Inventor: Alberto Fernandez Dell Oca, Montevideo (UY)

(73) Assignee: Siemens Aktiengesellschaft, Munich (DE)

( * ) Notice: Subject to any disclaimer, the term of this patent is extended or adjusted under 35 U.S.C. 154(b) by 10 days.

(21) Appl. No.: 13/266,140

(22) PCT Filed: Apr. 23, 2010

(86) PCT No.: PCT/EP2010/055437
§ 371 (c)(1),
(2), (4) Date: Jan. 19, 2012

(87) PCT Pub. No.: WO2010/122145
PCT Pub. Date: Oct. 28, 2010

(65) Prior Publication Data
US 2012/0106819 A1 May 3, 2012

Related U.S. Application Data

(60) Provisional application No. 61/172,721, filed on Apr. 25, 2009.

(51) Int. Cl.
*G06K 9/00* (2006.01)
*A61B 17/88* (2006.01)

(52) U.S. Cl.
USPC .......................................... 382/132; 606/281

(58) Field of Classification Search
USPC ......... 382/128, 129, 130, 131, 132, 133, 134; 378/4, 8, 21–27, 901; 600/407, 410, 600/411, 425, 427, 3, 7, 12, 30, 40, 300, 600/377; 128/920, 922
See application file for complete search history.

(56) References Cited

U.S. PATENT DOCUMENTS

| | | | |
|---|---|---|---|
| 6,382,835 B2 * | 5/2002 | Graumann et al. | 378/198 |
| 7,388,972 B2 * | 6/2008 | Kitson | 382/128 |
| 7,489,810 B2 * | 2/2009 | Owen | 382/128 |
| 7,831,096 B2 | 11/2010 | Williamson, Jr. | |

(Continued)

FOREIGN PATENT DOCUMENTS

| | | |
|---|---|---|
| EP | 1406203 A2 | 4/2004 |
| JP | 2008126063 A | 6/2008 |
| WO | 2005087125 A2 | 9/2005 |

*Primary Examiner* — Abolfazl Tabatabai
(74) *Attorney, Agent, or Firm* — Laurence A. Greenberg; Werner H. Stemer; Ralph E. Locher

(57) ABSTRACT

A method and a system assess a relative pose of an implant and a bone of a patient. The method includes: acquiring multiple medical X-ray images of the bone with the implant preliminarily mounted to the bone; providing a database of virtual 3D implant models and selecting the implant used; fitting the virtual implant to the medical X-ray image; selecting a bone model; and fitting the chosen bone model to the medical X-ray image. The system and method now allow directly in the operation room to assess the relative pose of the implant and the bone/bone fragments by a comparison of the medical image and the respective virtual image both having the same orientation in view. The resulting image is an image of the matching virtual 2D image of the implant used and the real medical image taken from the C-arm X-ray device.

16 Claims, 16 Drawing Sheets

(56) References Cited

U.S. PATENT DOCUMENTS

2005/0059873 A1 3/2005 Glozman et al.
2008/0118115 A1 5/2008 Williamson
2008/0269596 A1* 10/2008 Revie et al. .................. 600/424

* cited by examiner

10a

10b

10c

10d

10e

10f

METHOD AND A SYSTEM FOR ASSESSING THE RELATIVE POSE OF AN IMPLANT AND A BONE OF A CREATURE

The present application hereby claims the priority of the U.S. provisional application No. 61/172,721 filed Apr. 25, 2009. This application is hereby incorporated by reference.

BACKGROUND OF THE INVENTION

1. Field of the Invention

The present invention relates to a method and a system for assessing the relative pose of an implant and a bone of a creature.

2. Background

For the assessment of the relative pose of an implant and a bone of a creature usually X-ray images are used, in particular in a surgery environment when bone fragments have to be fixed in the correct pose. Usually, so-called C-arm systems are used which combine an X-ray source and a X-ray detector on a mobile cart having the form of the letter "C" allowing to rotate the X-ray source in the range of about at least 180° around a human patient or an animal. Nevertheless, since the C-arm device is mobile device, the image information contributes to a first control of what has been done by the surgeon but lacks precise information.

With the availability of X-ray computer tomography imaging (CT) and, of course, other image generating devices, like ultra-sound or magnetic resonance imaging (MRI), the possible shortcomings of the 2D C-arm information can be mitigated by post-operative CT scans for a precise assessment of the surgery results. Unfortunately, this means that patients have to undertake a re-surgery in order to reposition a bone fragment and/or the respective implant in case of mal-alignment or miss-placement of the implant. This problem has been addressed by the design of mobile CT scan machines which can be also used already in the operation room or mobile C-arms with 3D scan capabilities. These mobile CT scan machines do have clinical workflow limitations. Therefore, a real demand exists for providing 3D information in 2D X-ray images in the operation room.

To solve this problem, diverse software products exist which are designed to link information between medical image viewers (U.S. Pat. No. 7,489,810). This US patent discloses a method and a system for linking position (pose) information between two-dimensional (2D) and three-dimensional (3D) software applications for viewing diagnostic medical images. The position location information is integrated between 2D and 3D viewing paradigms. This integration provides directional communication between the 2D and 3D viewing paradigm systems. The 3D cursor allows for immediate synchronized navigation through different image sets such 3D magnetic resonance images and 2D images while they are being simultaneously viewed on the two different viewing applications. Further, diverse software products exist being designed to improve the X-ray diagnosis in breast cancer and lungs cancer computer assisted detection (CAD). However, there is still a demand for a computer assisted 3D detection of the implant position (pose estimation) during a surgery.

BRIEF SUMMARY OF THE INVENTION

It is therefore an objective of the present invention to provide a method and a system for assessing the relative pose of an implant and a bone of a creature already in the operation room which don't required any additional bulky equipment that has to be held and maintained in the operation room.

This objective is achieved according to the present invention with respect to the method by a method for assessing the relative pose of an implant and a bone of a creature, comprising the steps of:
a) acquiring one or multiple medical X-ray image(s) of the bone with the implant preliminarily mounted to the bone;
b) providing a database of virtual 3D implant models and selecting the implant used;
c) fitting the virtual implant to the medical X-ray image;
d) selecting a bone model; and
e) fitting the chosen bone model to the medical X-ray image.

With respect to the system this objective is achieved according to the present invention by a system for assessing the relative pose of an implant and a bone of a creature, comprising the steps of:
a) a medical imaging device for acquiring one or multiple medical X-ray image(s) of the bone with the implant preliminarily mounted to the bone;
b) a database comprising virtual 3D implant models and means for selecting the implant used;
c) a calculation means for fitting the virtual implant to the medical X-ray image;
d) means for selecting a bone model; and
e) the calculation means being further enabled to fit the chosen bone model to the medical X-ray image.

This system and this method now allow directly in the operation room to assess the relative pose of the implant and the bone/bone fragments by a comparison of the medical image and the respective virtual image both having the same orientation in view. With other words, the resulting image from the fitting steps is an image of the matching virtual 2D image of the implant used and the real medical image taken from the C-arm X-ray device both having the same pose thereby revealing whether the position of the bone/bone fragments relative to the implant in the patient is the exact position required or not. Corrections in the position as well for example in the depth of penetration of the bone by the mounting screws and/or other attachment means can be then effected immediately during the surgery. Of course, it is possible to take measurements in this overlayed image, such as measurement of angles of bone fragments relative to each other or of the bone relative to the implant.

Preferred embodiments of the present invention provide the method and the system having specific implementations of the method steps and the system components as mentioned above, wherein one or more of the following feature can be applied:
b1) For the fitting step, by selecting the implant used, a selection can be made of a set of virtual 2D images of the implant used out of the database, each virtual image being a reproduction of the virtual 3D implant model and a virtual 3D bone model taken from a different pose. Additionally, it is possible to generate intermediate pose virtual 2D images of the implant used for better fine-tuning of the following fitting step, alternatively the set of virtual 2D images could also be created online during the fitting process;
c1) fitting the virtual implant can be done by comparing the real medical X-ray image to the set of the generated virtual images in order with the aim to identify at least one virtual image showing a match of the pose of the 3D implant model in the 2D medical X-ray image with the implant in the virtual image. This matching virtual image can be aligned and visualized in the medical X-ray image, thereby linking the pose of the medical X-ray image and the 3D pose of the 3D implant model; and e1) in the resulting image it is possible to additionally insert virtual screws and/or other attachments for fixing the virtual implant according to the actual pose of the real implant and to compare the orientation and/or position of the virtual screws and/or other attachments with a desired position of the real screws and/or attachments prior to their insertion into the patient's bone.

It has to be mentioned at that occasion that various method can be used for accomplishing the fitting step. As mentioned above, it is possible to compare 2D images stored in the database against the real X-ray image. Alternatively, the fitting step can be also accomplished by using projection data of indicative features of the respective implants and analyse the real implant in the real X-ray image with respect to its indicative features, such as edge curvature, length and width dimensions, position of opening and/or bore holes relative to each other. Application of likelihood algorithm and/or Huffman or other entropy encoding algorithms is a common measure within this context.

In a further preferred embodiment of the present invention the step of comparing may be carried out by a comparison of an indicative structure feature of the implant in the at least one medical image to a corresponding indicative structure feature of the implant in the plurality of virtual images. For example, an indicative edge curvature or the like can be compared to the virtual images until a virtual image is found having the same or substantially the same pose of view as the medical image.

On the other hand, the step of comparing may be carried out by a pixel-wise comparison of the at least one medical image to the plurality of virtual images. This option just compares the pixels of medical image to the pixels of the virtual image.

In a further preferred embodiment of the present invention it can be foreseen that the identified matching virtual image is that image out of the plurality of virtual pictures having achieved the maximum number of congruent pixels during the comparison. Alternatively, the identified matching virtual image may be that image or those images out of the plurality of virtual pictures having achieved a number of congruent pixels during the comparison exceeding a predetermined threshold of congruent pixels.

In a further preferred embodiment of the present invention, the bone model can be calculated directly from a CT scan of the bone of interest or it can be calculated and mirrored from the CT scan of the contra-lateral side in case the bone of interest is fractured and bone fragments are displaced or the bone model can be taken from a database of statistical bone models, alternatively.

In order to accelerate the fitting step of the virtual implant to the real medical X-ray image, the fitting procedure may be accelerated by a knowledge of a C-arm projection geometry which can be optionally determined by a calibration step. In case, an image intensifier is used with the C-arm system as X-ray detector, an image calibration due to image intensifier distortions is necessary in order to convert the virtual implant into the dimension of the image intensifier or vice versa.

Preferred embodiments of the present invention are hereinafter explained in more detail with reference to the attached drawings.

DESCRIPTION OF THE INVENTION

Figure 1:
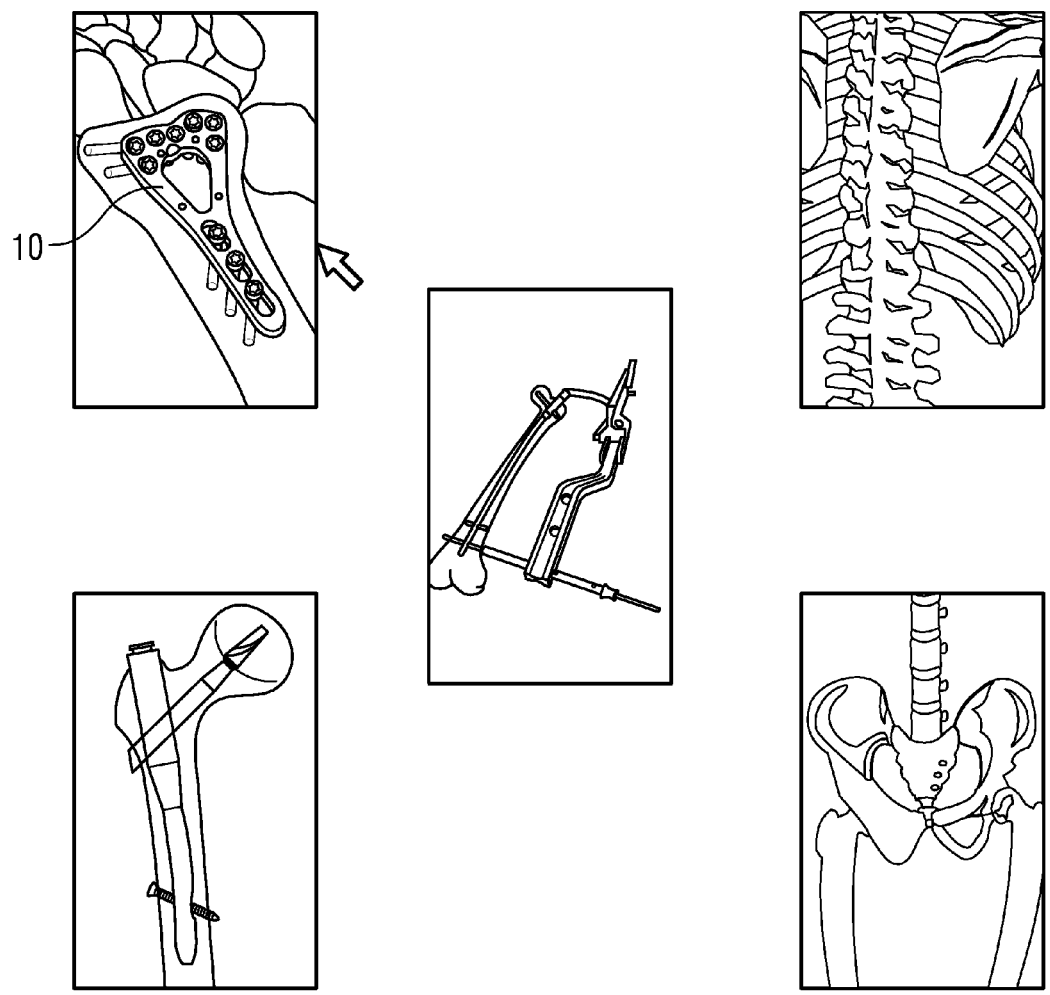
FIGS. 1 to 10 thereby illustrate the process of assessing the position of an implant in a bone surgery using the example of volar distal radius plates.

FIG. 1 illustrates the selection of the kind of implant to be used. In the present case, a volar distal radius plate is used in a radius bone surgery. Other possible implants are for example femoral nails.

Figure 2:
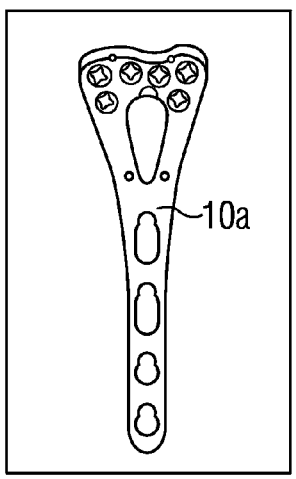
Figure 2:
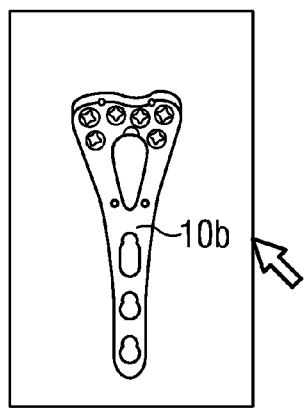
Figure 2:
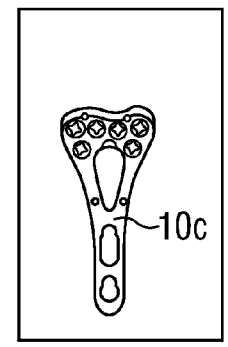
Figure 2:
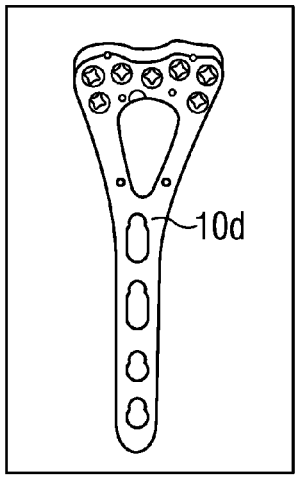
Figure 2:
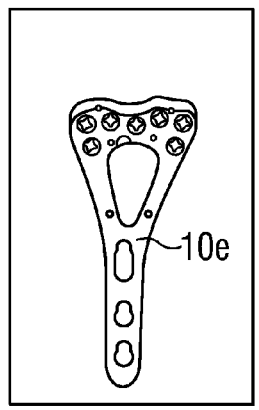
Figure 2:
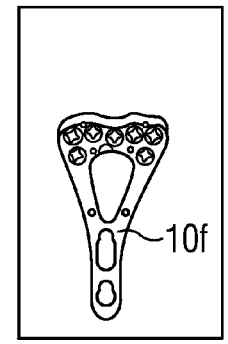

FIG. 2 illustrates the selection of the type of volar distal radius plate which will be used in the surgery from a database of possible radius plate implants 10a to 10f.

Figure 3:
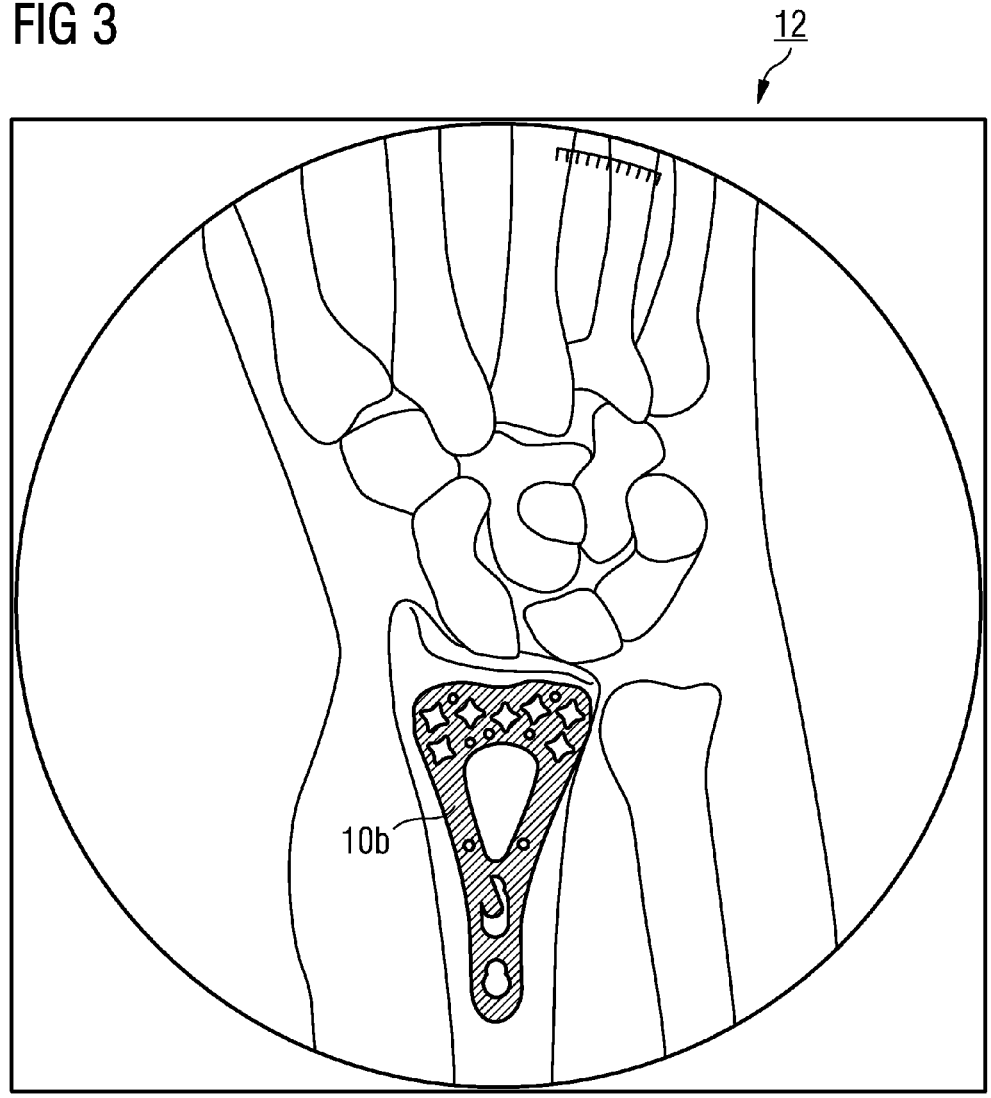

FIG. 3 illustrates the step of capturing a C-arm image 12 from the volar distal radius plate 10b which has been preliminarily attached to the bone of the patient during a surgery.

Figure 4:
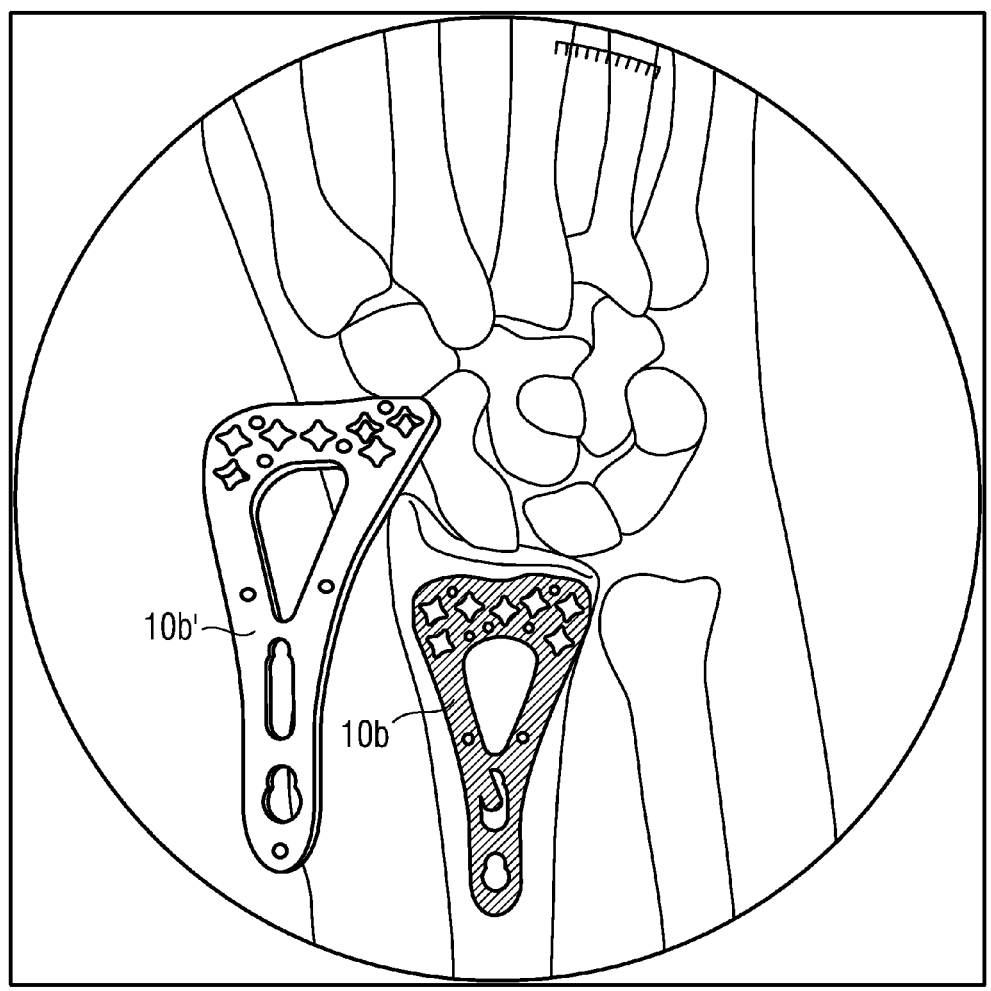

FIG. 4 illustrates the step of virtually adding the selected type of volar distal radius plate 10b' from the database to the patient's C-arm image. Currently, in the image the pose of the inserted virtual radius plate 10b' does not match the pose of the real radius plate implant 10b.

FIGS. 5a to 5d now show the step of linking the pose of the virtual radius plate to the real radius plate implant. During this process, different images of the virtual implant, each image taken at a different camera pose, are compared to the pose of the real radius plate implant 10b. Alternatively, it is possible to generate the virtual images of the virtual radius plate online during the surgery.

Figure 5A:
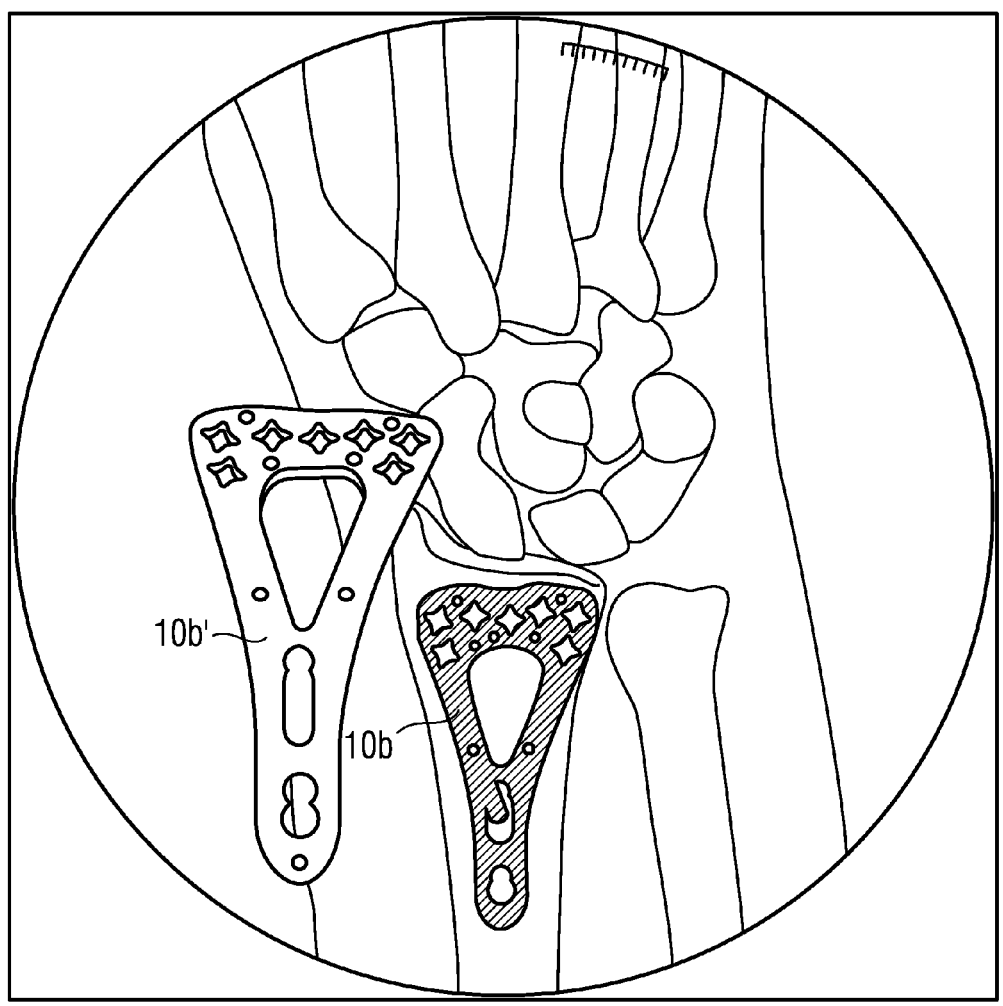
Figure 5B:
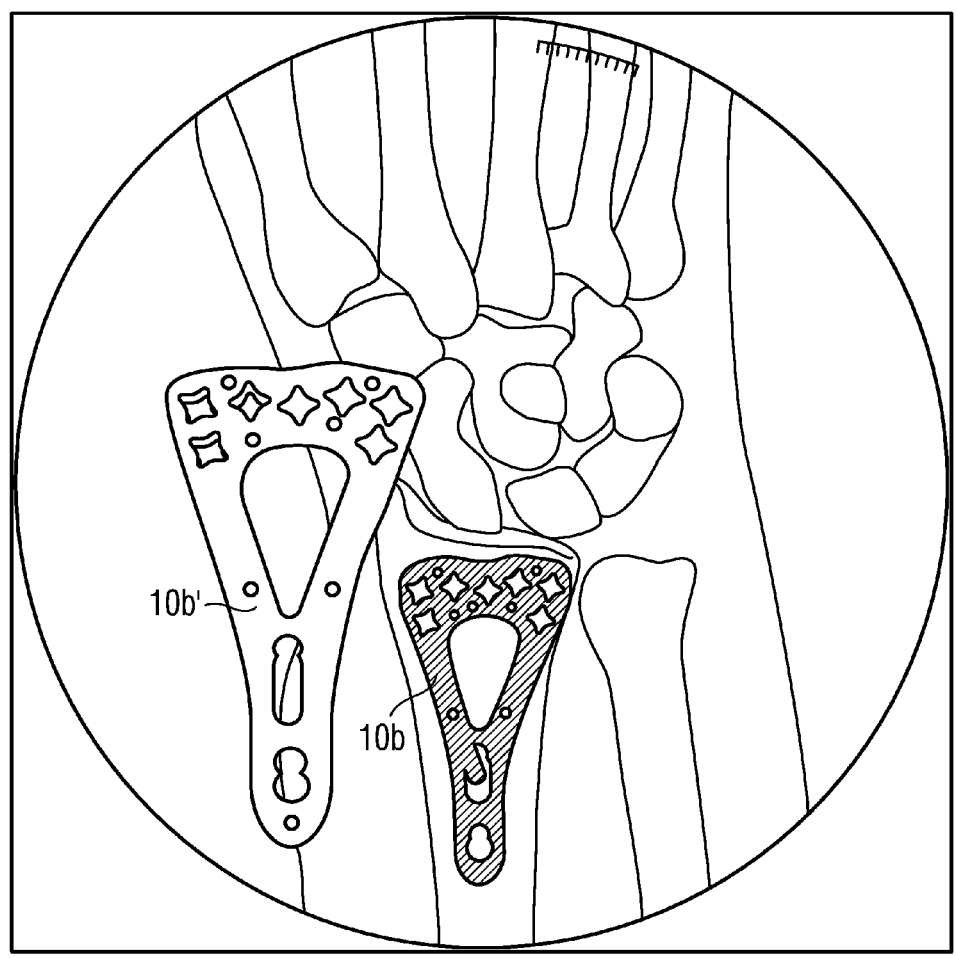
Figure 5C:
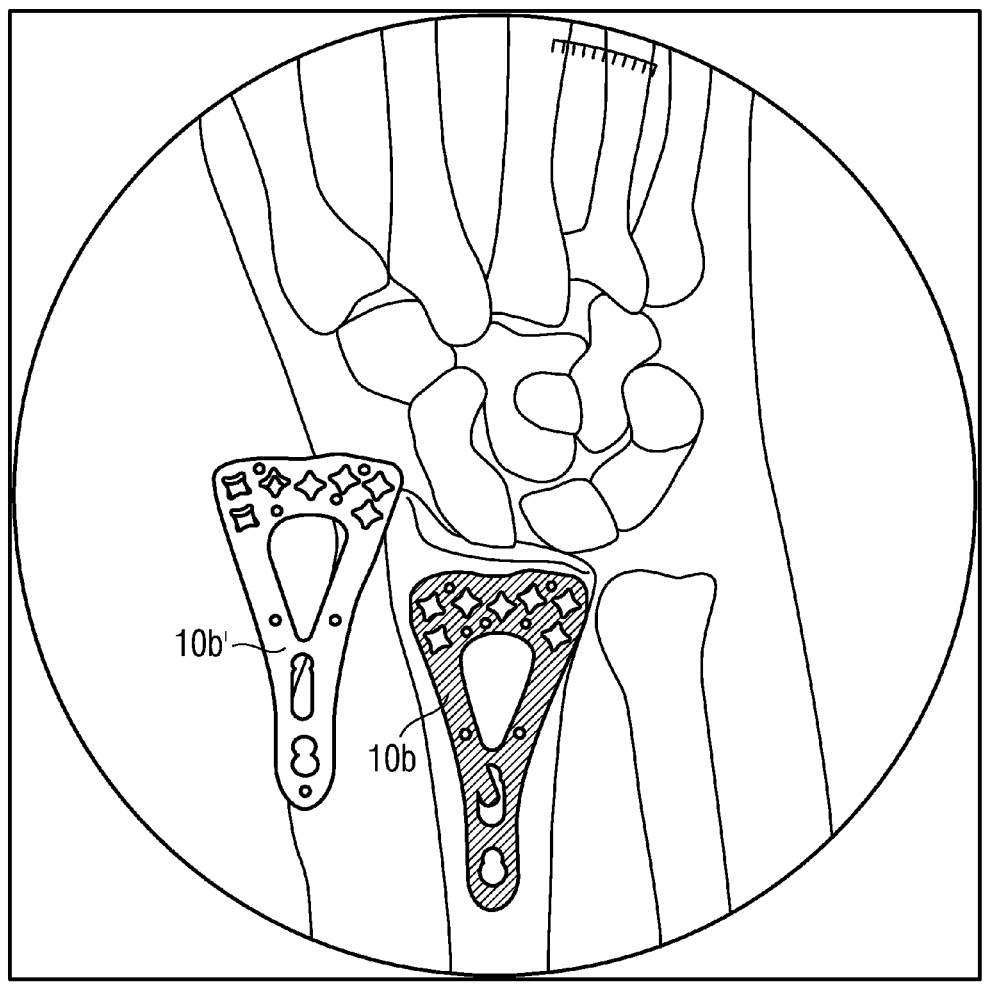
Figure 5D:
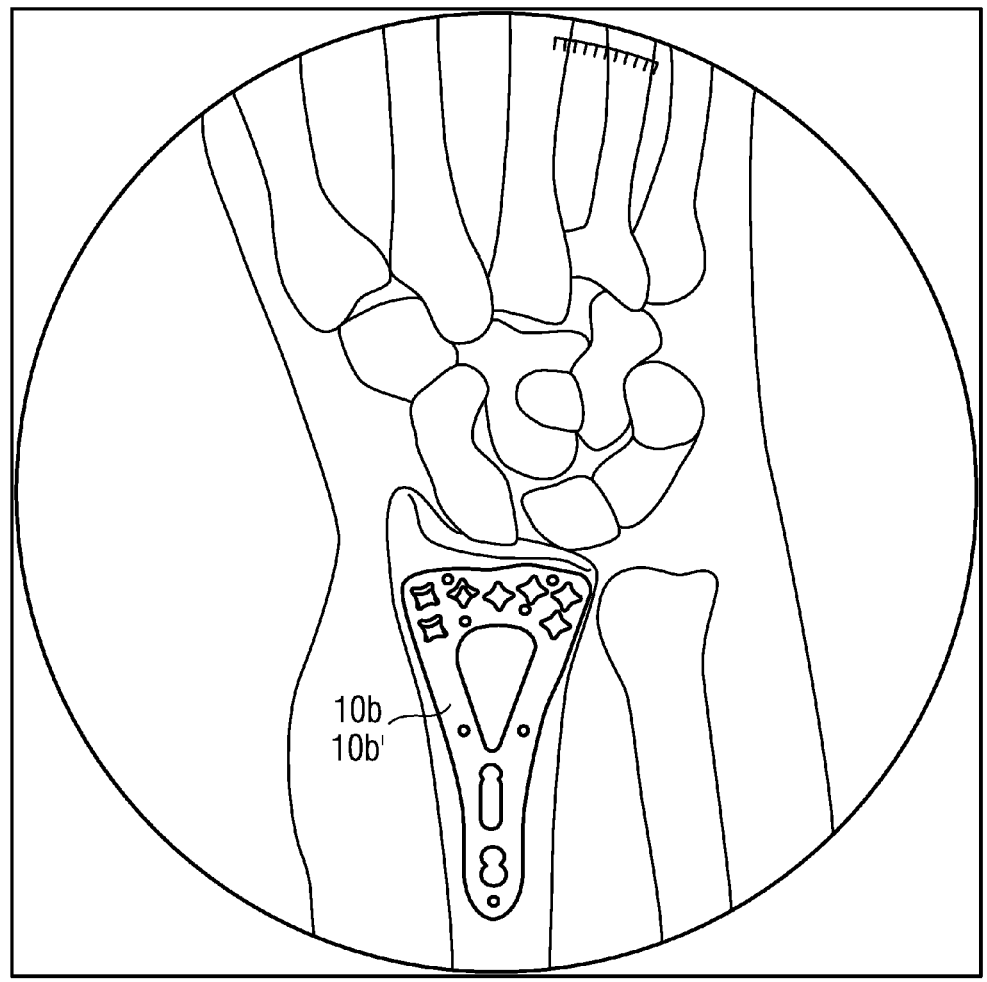

Further, it would be also an option to calculate intermediate pose virtual image of two virtual image having adjacent pose (interpolation). FIG. 5d shows the exact match of the pose of the best matching image out of the set of the virtual radius plate images and the real radius plate implant.

Figure 6A:
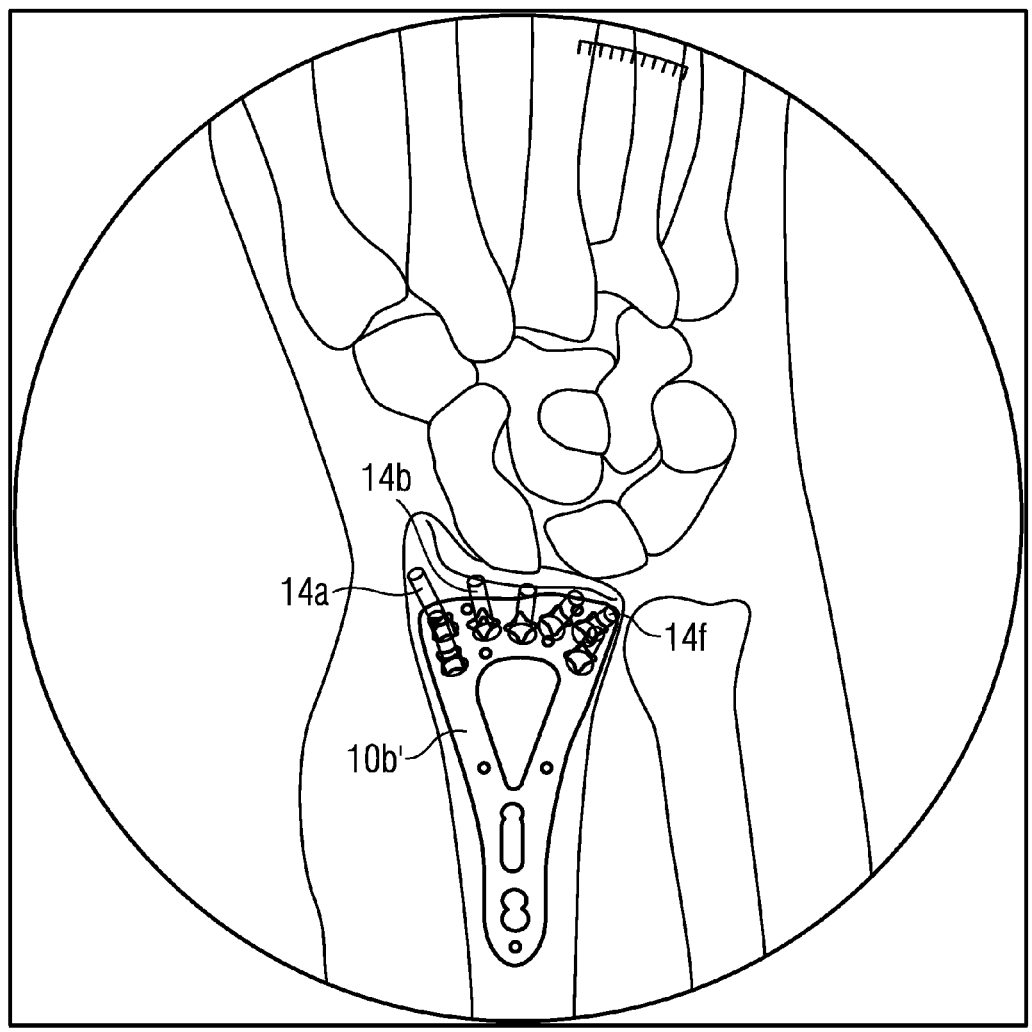
Figure 6B:
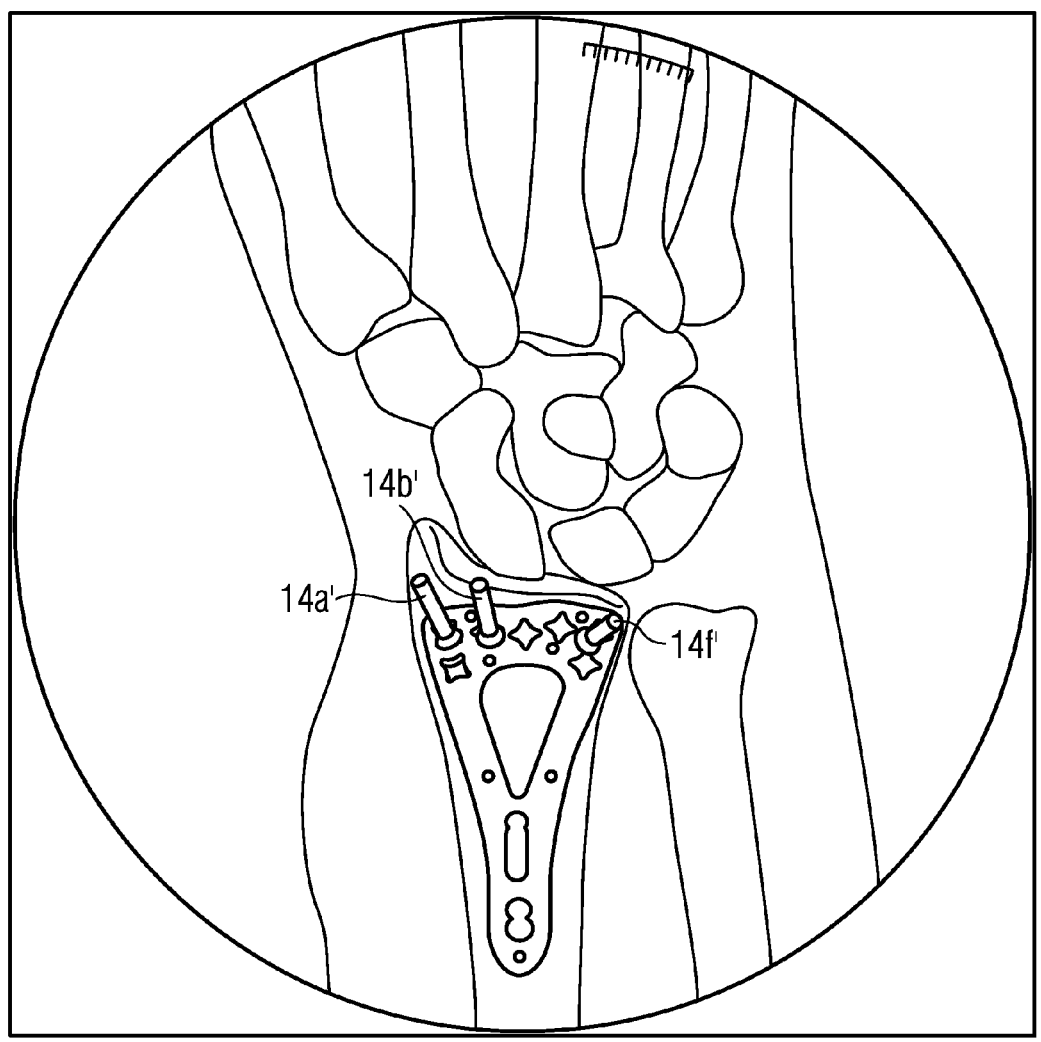

FIGS. 6a and 6b show in the following in the surgery process the step of virtually inserting the positions of virtual screws 14a', 14b' and 14f' in case they would be attached to the patient's bone at the current position of the radius plate 10b. FIG. 6b in particular illustrates that the virtual screws 14a', 14b' and 14f are far from the ideal position. The ideal positions are thereby derived from a simulation of the used implant and a virtual bone having (average) dimensions. Of course, a morphable bone model and/or pre-operative CT images can be used within this step as well.

Figure 7:
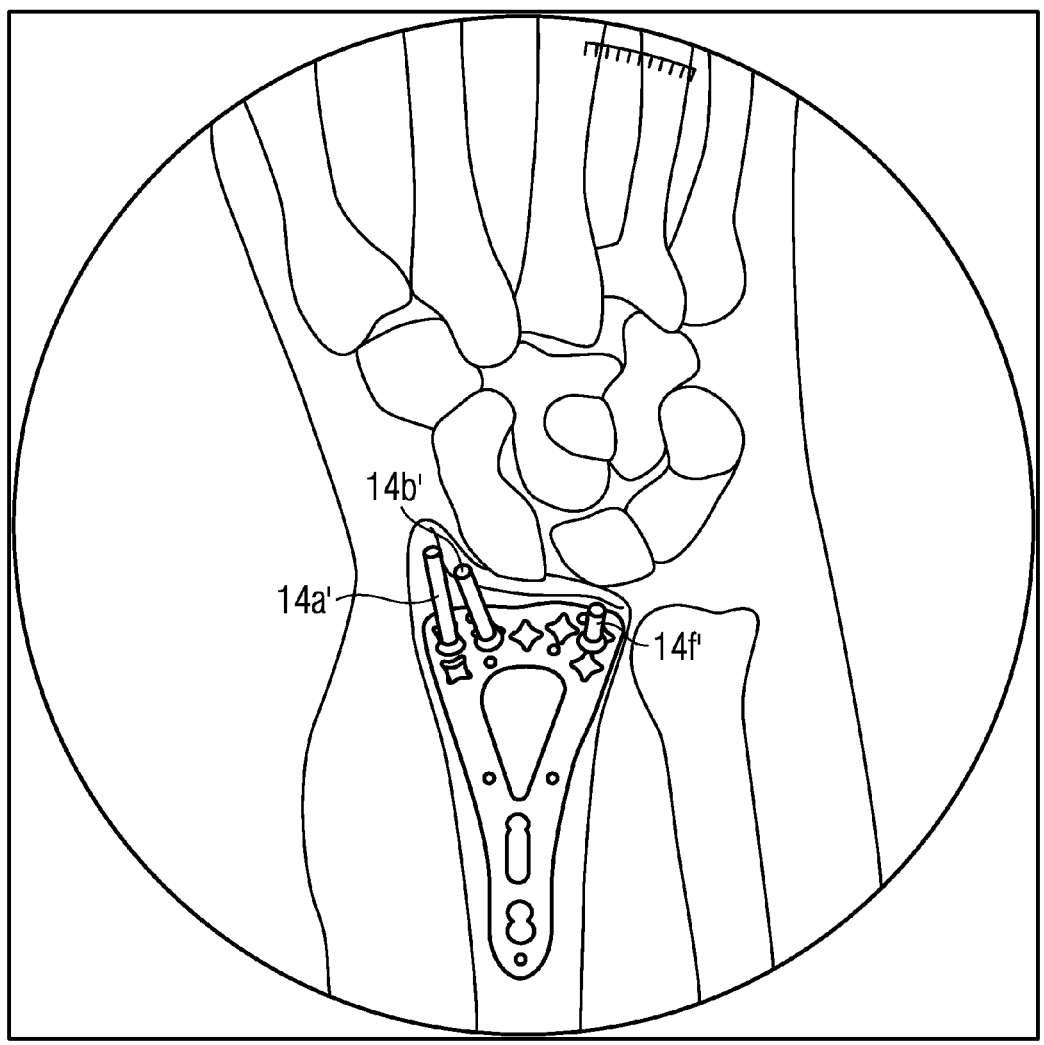

FIG. 7 illustrates the next step in the surgery process wherein VA locking plates helps to position the screws in an optimal position.

Figure 8:
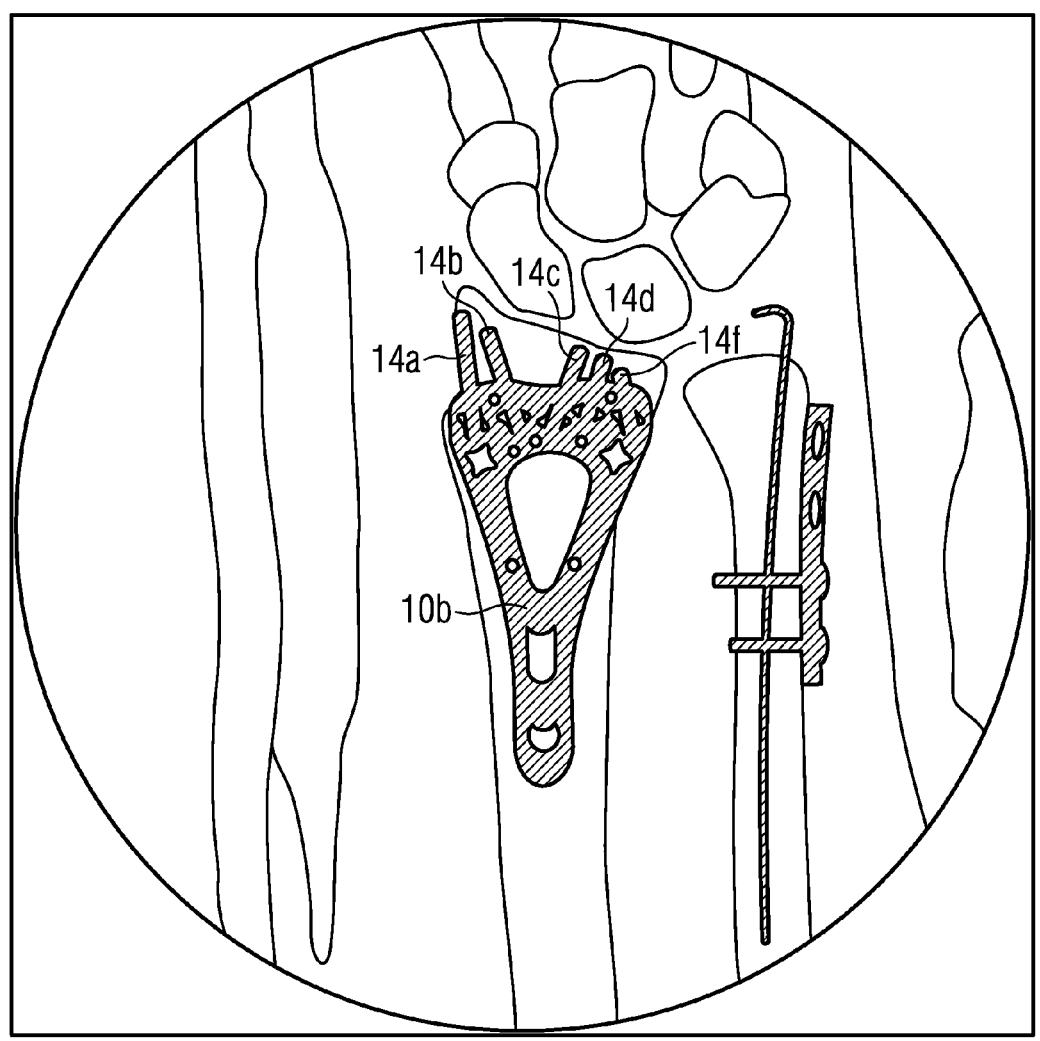

In FIG. 8 the situation is shown for the C-arm image after the real screws 14a, 14b and 14f (as well as 14c, 14d and 14e) are inserted into the bone of the patient according to the orientation derived from FIGS. 6 and 7.

Figure 9:
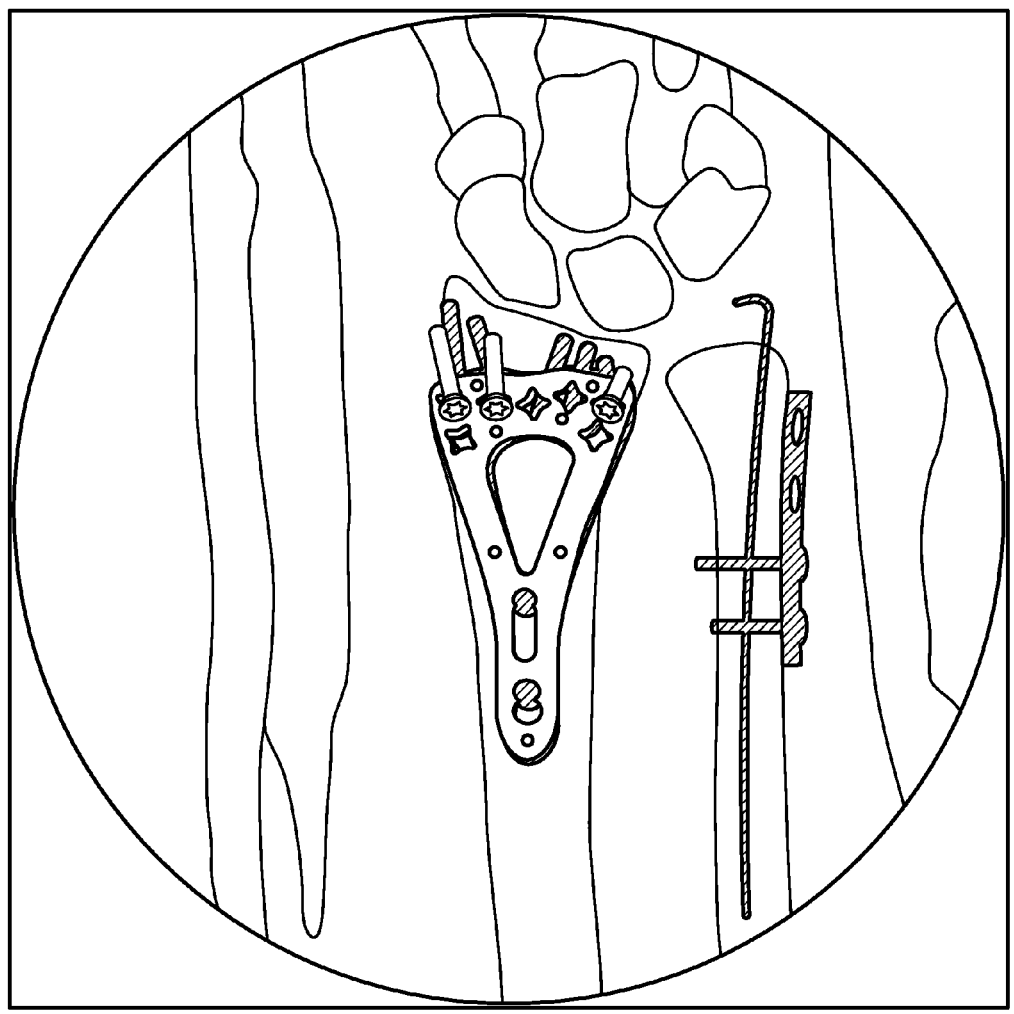

FIG. 9 shows an overlaying of the real C-arm image of the real radius plate implant and the real patients bone as compared to the virtual image of the virtual radius plate and the virtual screws in optimal position. This image gives the surgeon the final assessment of the position of the real screws as compared to the position of the virtual screws in optimal position/orientation.

Figure 10:
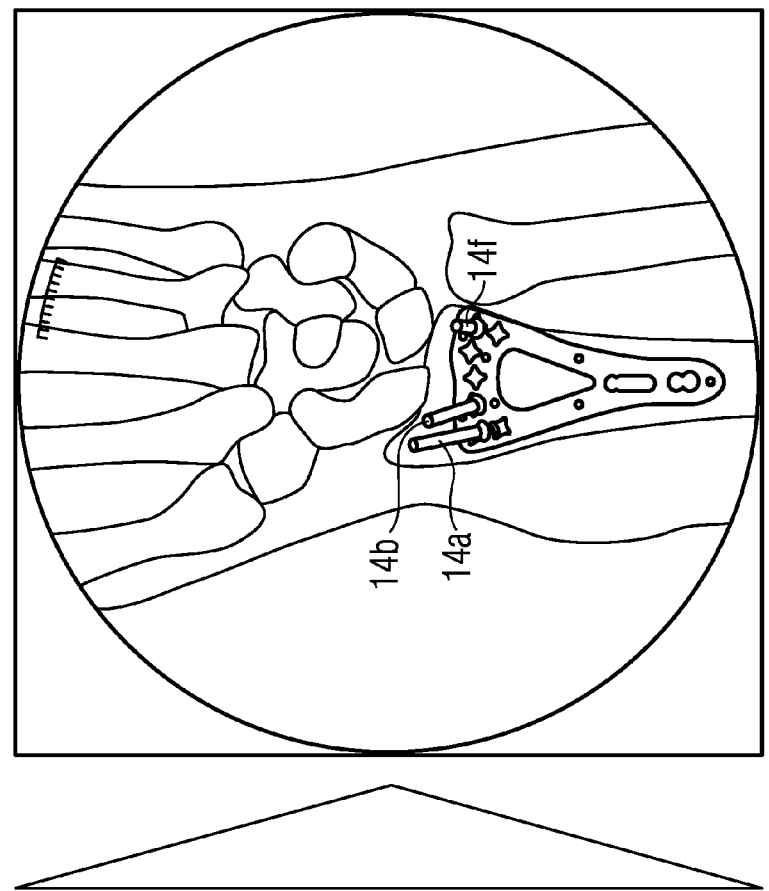
Figure 10:
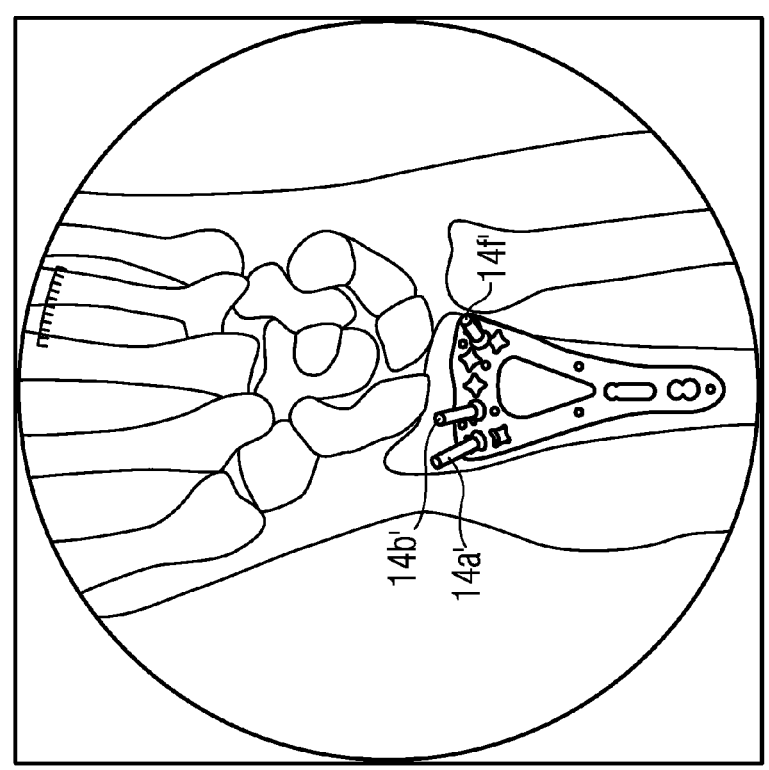

FIG. 10 shows now on the left side the image comprising the virtual screws 14a', 14b' and 14f in its virtual pose without any position-correcting activities by the surgeon. The image on the right side displays the real situation regarding the position and the orientation of the real screws 14a, 14b and 14f after the intervention of the surgeon by using the VA locking plates in order to optimize the position of the screws.

Figure 11:
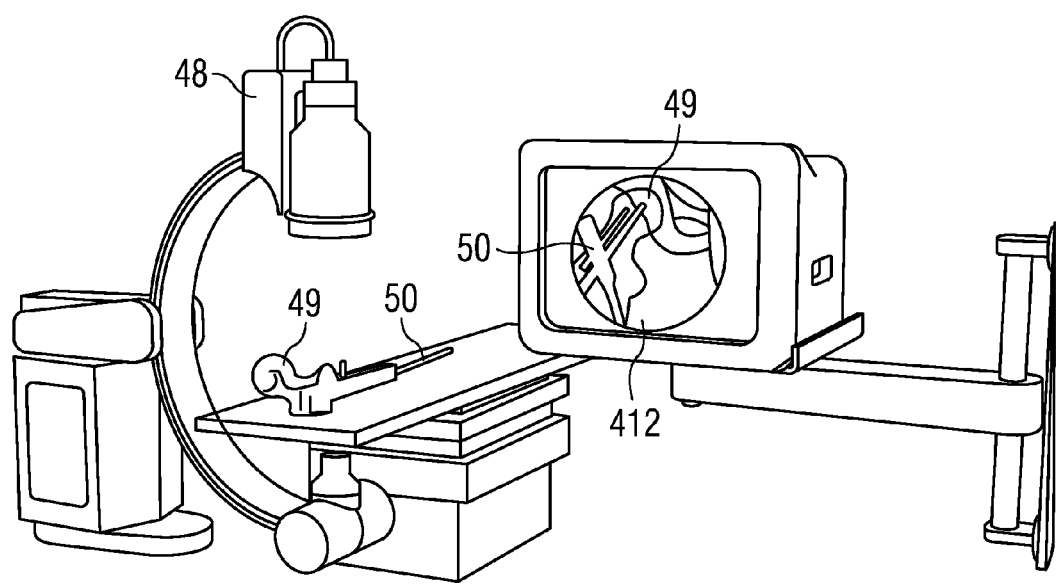
FIG. 11 represents a typical operation room environment.
Figure 11:
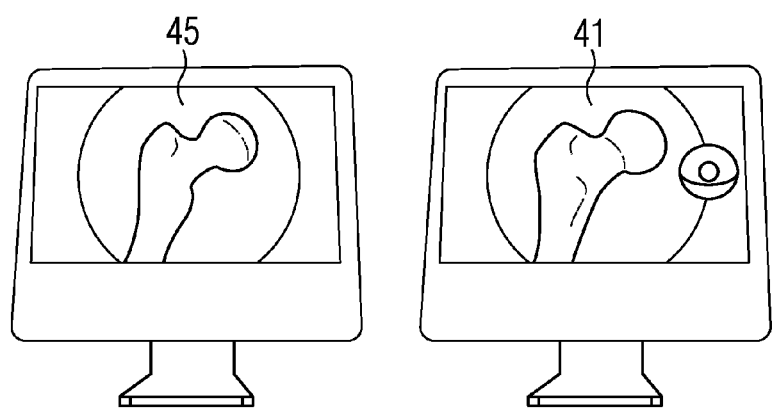

FIG. 11 now represents schematically a typical operation room environment. A C-arm system 48 is imaging a C-arm image 412 of a real bone 49 and an implant 50. In the workflow, the image 412 is reproduced as an image 45 in reproduced simulated radiation mode. A virtual image 41 shows a virtual bone having the same pose as the real bone shown the reproduced image 45.

Figure 12:
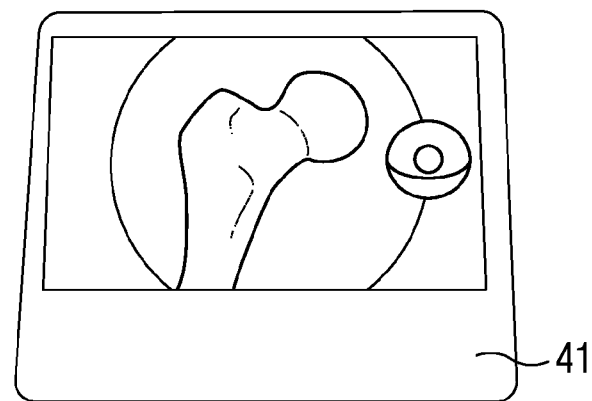
FIG. 12 represents a typical workflow in term of the visualized pictures on the display device aligned with a C-arm system.
Figure 12:
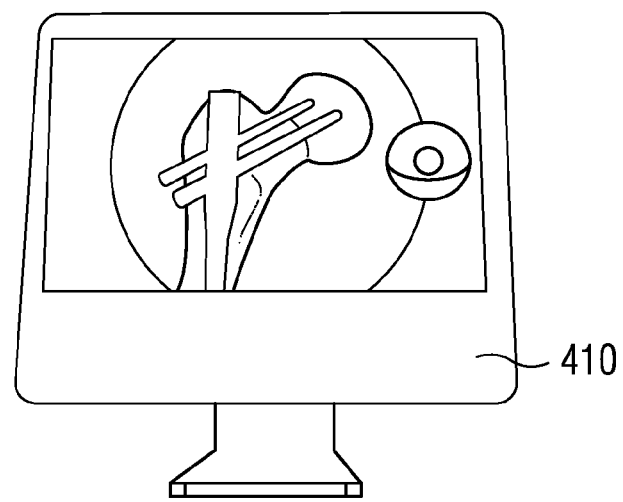
Figure 12:
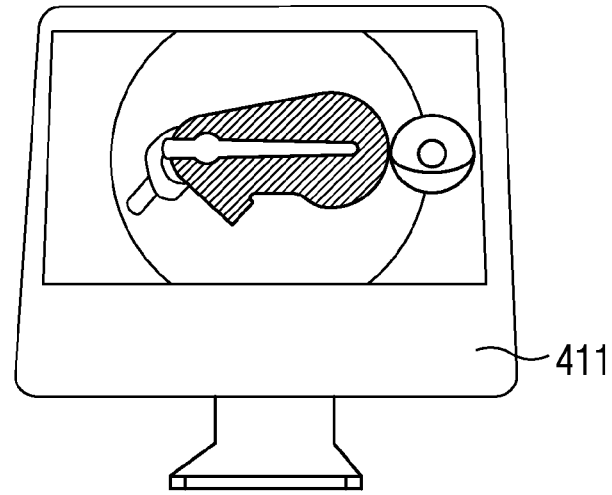

FIG. 12 shows now the workflow when using the matching images 41 and 45. By means of the data sets of the virtual bone and the virtual implant stored in the database of the C-arm system, the pose of the virtual bone and virtual implant image 410 is aligned with the pose of the real C-arm image 412 showing the real implant 50 and the real bone 49.

A final image 411 now enables the surgeon to assess the relative position of the virtual implant and the virtual bone by choosing the desired pose. Additionally, attachment means like screws and plates are shown in this image to give the surgeon a suggestion on an ideal position of both the implant and the attachments means as compared to the position of the implant 50 in the real C-arm image 412.

Remarkably, the inventive system and method already assist the surgeon during the surgery prior to the steps of the insertion of the screws into the bone(s) of the patient. Time for the recovery from the bone fracture and the comfort of the patient are increased significantly by the application of the method described above and the system used.

The invention claimed is:

1. A method for assessing a relative pose of an implant and a bone of a patient, which comprises the steps of:
   a) acquiring at least one medical X-ray image of the bone with the implant preliminarily mounted to the bone;
   b) providing a database of virtual 3D implant models and selecting the implant for use;
   c) fitting a virtual implant to the medical X-ray image;
   d) selecting a bone model; and
   e) fitting the bone model chosen to the medical X-ray image.

2. The method according to claim 1,
   b1) wherein by selecting the implant used a selection is made from a set of virtual 2D images of the implant used, each of the virtual 2D images being a reproduction of a virtual 3D implant model and a virtual 3D bone model taken from a different pose;
   b2) generating intermediate pose virtual 2D images of the implant for better fine-tuning of the fitting step;
   c1) fitting the virtual implant by comparing the medical X-ray image to a set of virtually generated images in order to identify at least one virtual image showing a match of a pose of the 3D implant model in the medical image with the implant in the virtual image and aligning and visualizing the medical X-ray image with an identified matching virtual image, thereby linking the pose of the at least one medical X-ray image and a 3D pose of the virtual 3D implant model; and
   e1) inserting at least one of virtual screws or other attachments for fixing the virtual implant according to an actual position of a real implant and comparing at least one of an orientation or a position of the virtual screws or the other attachments with a desired position of real screws prior to insertion into the bone of the patient.

3. The method according to claim 2, which further comprises carrying out the step of comparing in c1) by a comparison of an indicative structure feature of the implant in the at least one medical X-ray image to a corresponding indicative structure feature of the implant in the plurality of virtual images.

4. The method according to claim 3, wherein an identified matching virtual image is the virtual image out of the plurality of virtual images having achieved a maximum number of congruent pixels during a comparison.

5. The method according to claim 3, wherein an identified matching virtual image is the image out of the plurality of virtual images having achieved a number of congruent pixels during a comparison exceeding a predetermined threshold of congruent pixels.

6. The method according to claim 2, which further comprises carrying out the step of comparing in c1) by a pixel-wise comparison of the at least one medical X-ray image to the plurality of virtual images.

7. The method according to claim 1, which further comprises:
   performing one of:
   calculating the bone model directly from a CT scan of the bone of interest; or
   calculating and mirroring the bone model directly from the CT scan of a contralateral side in case the bone of interest is fractured and bone fragments are displaced or the bone model is taken from a database of statistical bone models.

8. The method according to claim 1, which further comprises accelerating the fitting step via knowledge of a C-arm projection geometry which can be determined by a calibration step.

9. A system for assessing a relative pose of an implant and a bone of a patient, the system comprising:
   a medical imaging device for acquiring at least one medical X-ray image of the bone with the implant preliminarily mounted to the bone;
   a database containing virtual 3D implant models and means for selecting the implant in use;
   a calculation device for fitting the virtual implant to the medical X-ray image;
   means for selecting a bone model; and
   said calculation device enabled to fit the bone model chosen to the medical X-ray image.

10. The system according to claim 9, wherein:
    by selecting the implant used a selection is made out of said database having virtual true to real world scale 3D implant models of a set of virtual 2D images of the implant used, each of the virtual 2D images being a reproduction of the virtual 3D implant model and a virtual 3D bone model taken from a different pose and generating intermediate pose virtual 2D images of the implant used for better fine-tuning;
    said computing device for performing the fitting compares the medical X-ray image to a set of virtually generated images to identify at least one virtual image showing a match of the pose of the 3D implant model in the medical X-ray image with the implant in the virtual image and said computing device aligning and visualizing the medical X-ray image with an identified matching virtual image, thereby linking the pose of the at least one medical X-ray image and the 3D pose of the 3D implant model; and
    said computing device inserting at least one of virtual screws or other attachments for fixing the virtual implant according to an actual position of a real implant and comparing at least one of an orientation or a position of the virtual screws or the other attachments with a desired position of real screws prior to their insertion into the bone of the patient.

11. The system according to claim 10, wherein a comparison is carried out by a comparison of an indicative structure feature of the implant in the at least one medical X-ray image to a corresponding indicative structure feature of the implant in the plurality of virtual images.

12. The system according to claim 11, wherein an identified matching virtual image is the image out of the plurality of virtual images having achieved a maximum number of congruent pixels during the comparison.

13. The system according to claim 11, wherein an identified matching virtual image is at least one image out of the plurality of virtual images having achieved a number of congruent pixels during the comparison exceeding a predetermined threshold of congruent pixels.

14. The system according to claim 10, wherein a comparison is carried out by a pixel-wise comparison of the at least one medical X-ray image to a plurality of virtual images.

15. The system according to claim 9, wherein the bone model is calculated directly from a CT scan of the bone of interest or is calculated and mirrored from the CT scan of a contra-lateral side in a case the bone of interest is fractured and bone fragments are displaced or the bone model is taken from a database of statistical bone models.

16. The system according to claim 9, wherein the fitting step is accelerated via knowledge of a C-arm projection geometry which can be determined by a calibration step.

* * * * *